US005731325A

United States Patent [19]
Andrulis, Jr. et al.

[11] Patent Number: 5,731,325
[45] Date of Patent: Mar. 24, 1998

[54] TREATMENT OF MELANOMAS WITH THALIDOMIDE ALONE OR IN COMBINATION WITH OTHER ANTI-MELANOMA AGENTS

[75] Inventors: Peter J. Andrulis, Jr., Bethesda; Murray W. Drulak, Gaithersburg, both of Md.

[73] Assignee: Andrulis Pharmaceuticals Corp., Bethesda, Md.

[21] Appl. No.: 471,353

[22] Filed: Jun. 6, 1995

[51] Int. Cl.$^6$ ........................ A61K 31/445; A61K 31/175
[52] U.S. Cl. ............................................. 514/323; 514/589
[58] Field of Search ..................................... 514/323, 589

[56] References Cited

U.S. PATENT DOCUMENTS 5,399,363   3/1995   Liversidge et al. ................... 424/490

OTHER PUBLICATIONS

Carter et al, Chemotherapy of Cancer, 2nd Ed John Wiley & Sons, N.Y., N.Y., 1981, pp. 101 and 209.

*Primary Examiner*—Jerome D. Goldberg
*Attorney, Agent, or Firm*—Isaac A. Angres

[57] ABSTRACT

A method for treatment of malignant melanoma by administering an effective amount of thalidomide alone or in combination with other anti-melanoma drugs.

2 Claims, No Drawings

TREATMENT OF MELANOMAS WITH THALIDOMIDE ALONE OR IN COMBINATION WITH OTHER ANTI-MELANOMA AGENTS

The present invention is directed to compositions and methods for treating malignant melanoma. In one specific aspect, the present invention is directed to a method for treating melanomas with thalidomide. In another specific embodiment of the invention, melanoma is treated with thalidomide in combination with other anti-melanoma drugs.

The present invention also relates to methods of treating melanomas with cytokine/growth factor inhibitors such as those agents inhibitory to basic fibroblast growth factor (bFGF), TNF-alpha, IL-1 and/or melanoma growth stimulatory activity (MGSA) factor as well as pharmaceutical compositions containing relevant cytokine/growth factor inhibitors and/or other anti-melanoma drugs.

DESCRIPTION OF THE PRIOR ART

Thalidomide was first synthesized and marketed in the 1950's as a sedative. The toxicity of the compound was so low that a dose killing 50% of animals ($LD_{50}$) could not be established. Thalidomide was therefore thought to be a safer alternative to barbiturates. In 1961, thalidomide administered to pregnant women resulted in an epidemic of congenial malformations. The incidence of malformed babies paralleled the sales of thalidomide and quickly dropped off when thalidomide was removed from the market.

Oral administration of thalidomide in the range of 100–200 mg in adult humans results in a peak blood level of 0.9–1.5 mg/liter after 4–6 hours. Hydrolytic cleavage of thalidomide occurs in vitro, the rate of which increases as the pH increases. However, hydrolytic cleavage of thalidomide in serum at pH 7.4 is much slower than in vitro at pH 7.4. This may be due to thalidomide being highly bound to plasma proteins. Studies in animals demonstrated high thalidomide concentrations in the gastrointestinal tract, liver and kidneys with lower concentrations in muscle, brain and adipose tissue. In pregnant animals, thalidomide can pass across the placenta.

Although a complete study of thalidomide metabolism in humans has not been performed, in animals the main pathway for thalidomide breakdown appears to be nonenzymatic hydrolytic cleavage. Even though immunodulatory effects of thalidomide have not been clearly defined at the molecular level, thalidomide has been used to treat the following immunologically based diseases: acute and chronic Graft vs Host Disease, aphthosis, cold hemagglutinin disease, erythema nodosum leprosum, erythema multiform, histiocytosis, immune complex vasculitis, Jessner-Kanofs Disease, lichen planus, pemphigoid disorders, photodermatoses, prurigo nodularis, pyoderma gangrenosum, rheumatoid arthritis, sarcoidosis, and Weber-Christian Disease.

Melanomas are any group of malignant neoplasms primarily of the skin that are composed of melanocytes. Most melanomas develop from a pigmented benign congenital skin blemish termed a nevus over a period of several months or years and occur most frequently in fair skinned people having light colored eyes. Melanomas occur as black or brown spots having an irregular border, pigment appearing to radiate beyond the border width and/or a red, black, or blue coloration observable on close examination. Sometimes a nodular surface is suggestive of a melanoma. Different types of melanomas include, but are not limited to: amelanotic, benign juvenile, lentigo maligna, primary cutaneous, and superficial spreading. A number of steps describing lesional progression to metastaric melanoma include: 1) a common melanocytic nevus without cytological or architectural atypia, 2) melanocyte nevus with persistent architectural atypia, 3) dysplastic nevus with cytological and architectural atypia, 4) radial growth phase of primary melanoma with no ability to metastasize, 5) vertical growth of the primary melanoma with the ability to metastasize, and 6) metastic melanoma.

Melanoma in its advanced stages is an incurable disease. Seventy-five percent of skin cancer death in the United States are due to malignant melanoma (Cancer Manual, Sixth Edition, (1982); American Cancer Society, Boston, p. 104). Worldwide incidence has been rising sharply, doubling every decade over the past 30 years.

Surgery is only a curative therapy for melanoma in its early stage; if used aggressively for local recurrence or metastatic disease to regional nodes, it is associated with only 20%–30% cure rate. The role of surgery in advanced diseases is palliative.

In most instances, melanoma is considered radioresistant and radiotherapy is used mostly for palliation. The use of hormonal therapy has been disappointing. Chemotherapy has resulted in some partial remissions with a single agent response rate for DTIC (dimethyltriazenoimidazale carboxamide—also known as Dacarbazine) of 24% (Roth and Kirkwood (1987), *Cur. Top. Oncology* 9 (5): 2–11). DTIC is considered the most effective single agent for the treatment of metastatic melanoma although visceral metastases involving the gastrointestinal tract, the liver, and the brain are relatively less responsive than soft tissue disease. Hematologic and GI toxicities vary with the DTIC dose regimen used but antitumor schedule dependency has not been observed. Although not widely studied in melanoma, five-day continuous infusions seem to be a rational compromise, exhibiting the least acute toxicity while maintaining an equivalent dose response. Multidrug combination regimens when compared in randomized prospective trials have not shown statistically significantly better response rates than DTIC alone. (De Vita, V. T., Jr., et al., eds. (1985) *CANCER, Principles & Practice of Oncology.*, 2nd ed., p. 1406).

Although the total spontaneous regression of melanoma has been reported on rare occasions, partial spontaneous regression is a regularly recognized phenomenon. This suggests that an immunologic event occurs with regularity in the disease. Pathologists frequently describe an intense mononuclear cell infiltrate beneath many melanomas suggestive of this immune response (*Cancer Rates and Risks*, 3rd Ed. (1985), NIH Pub. No. 85–691:99).

Earlier studies using immunotherapy in melanoma have been disappointing. Local immunotherapy with bacille Calmette-Guerin (BCG) showed greatest response in patients with small tumor burdens limited to the dermis. Visceral metastases did not respond and there was, at best, a minor effect on survival. However, much renewed interest in this modality of therapy has been aroused by the discovery of a wide range of immunomodulatory agents. Interferon is in clinical trials and has shown limited but definite efficacy to date (Creagan, E. T., et all. (1986) *Cancer Treatment Rep* 70(5):619–624).

For successful specific immunotherapy, the existence of an immunogenic tumor-associated antigen is required. This is a difficult requirement in humans because many human cancers have low immunogenicity. Although there has been some success in preparing melanoma vaccine, some studies have shown that human melanomas only rarely stimulate autologous lymphocytes. The reasons for this lack of stimulatory activity are not well understood. Some investigators have shown a suppression of lymphocyte activity by tumor-derived factors (Roth, J. A., et al. (1983) *J. Immunol* 130:303–308).

Certain growth factors or hormones have been implicated in the proliferation of melanomas such as melanoma growth stimulating activity (MGSA) factor, a normal regulator of cellular proliferation in a variety of cell types which appears to be produced in an deregulated manner in melanoma cells during tumor progression. MGSA m-RNA is not detected in normal melanocytes but, in transfection experiments with normal melanocytes that result in constitutive expression of MGSA, the melanocytes develop a transformed phenotype. MGSA produced by melanoma cells can act through a paracrine as well as autocrine loop since these cells have MGSA factor receptors on their surface. Such MGSA not only stimulates the growth of melanoma cells but also recruits neutrophils and lymphocytes to the site, which in turn produce factors such as TNF-alpha and IL-1. Endothelial cells stimulated by IL-1 and TNF-alpha can produce MGSA which may in turn have a paracrine proliferative effect on melanoma cells [Wen, Roland, and Derynck, *EMBO. J.* 8:1761–66 (1989), Richmond, *Seminar Dermatol* 10:246–55 (1991)]. Thalidomide has been demonstrated to be an inhibitor of IL-1 (Shannon et al., *American Society for Microbiology Annual Meeting*, Abs. U-53, 1990) and TNF-alpha (Sampaio et al., *J. EXP. Med.*, 173: 699–703, 1991) synthesis. Another growth factor, bFGF is of prime importance in the proliferation of melanomas. There is evidence that bFGF is an important autocrine growth factor for melanoma cells [Moscatelli et al., *J. Cell Physical*, 129:273–6 (1986); Halaban et al., *Oncogene Res.* 3:177–86 (1988)] bFGF has been demonstrated to stimulate the growth of melanoma cells when added exogenously (Richmond et al., *Cancer Res.* 42: 3175–80, 1982) and bFGF has been detected in melanoma tissue from humans (Lobb et al., *J. Biol. Chem.* 261:1924–26, 1986). In one study, quantitative RIA for bFGF and [$^{125}$I] bFGF binding assay showed that all six melanoma cell lines tested had manufactured bFGF and expressed a high affinity bFGF receptor (Kato et al., *Melanoma Res.* 2:13–23, 1992). This is consistent with the findings of a number of other groups [Herlyn et al., *Adv. Cancer Res.* 54:213–234 (1990); Halaban et al. *Oncogene Res.* 3:177–86 (1988)]. In the same study, when an antisense oligonucleotide to the initiation site of bFGF coding region was introduced into melanoma cell lines, there was an inhibition of multiplication. This further indicated that proliferation of melanoma cells is at least under partial autocrine control of bFGF. bFGF also was demonstrated to have an additive proliferative effect on melanoma cells when such cells were exposed simultaneously to bFGF and other growth factors such as insulin like growth factor I (IGF-I), epidermal growth factor (EGF) and transforming growth factor alpha (TGF-alpha). This leads us to propose suitable and effective therapeutic approaches for melanomas involving a combination therapeutic regimen consisting of agents that separately inhibit these different growth factors. Justifications of this invention include combining the approach of, e.g., Pollak et al., *J. Natl. Cancer Institute* 82:1693–7 (1990) who reported that Tamoxifen treatment resulted in reductions in IGF-1 levels in breast cancer patients, with that of D'Amato et al., *Proc. Natl. Acad. Sci.* 91:4082–4085 (1994), who demonstrated that thalidomide administered orally was an effective inhibitor of anglogenesis induced by bFGF in the rabbit cornea micropocket assay. Since it is well known that in order for melanoma to develop and spread, bFGF-induced growth and angiogenesis, respectively, must take place, the potential exists for an effective combination therapy for melanoma patients involving thalidomide and Tamoxifen. Therefore, we propose using thalidomide alone or in combination with other therapies to inhibit the production and/or activities of cytokine/growth factors such as TNF-alpha, IGF-1, EGF, TGF-alpha, IL-1 beta, MGSA and bFGF in different cell types involved in tumor growth and/or anglogenesis.

To this point a number of different single agents and combination treatments have been used to treat malignant melanomas with only limited success. Single agent therapies include: Dacarbazine, Nitrosoureas, Detrorubicin, Taxol, Vindesine, and Dibromodulcitol. However, the overall response rate to these single therapies ranges from 15 to 22% (McClay and Mastrangelo, *Seminars in Oncology* 15: 569–77, 1988). Commonly employed combination therapies are as follows:

1) DBPT which consists of: Dacarbazine (DTIC); BCNU (which is 1, 3- bis-[2-chloroethyl-1-nitrosourea); cisplatin; tamoxifen.

2) CBC which consists of: CCNU (which is (1-[2 chloroethyl]-3-cyclohexyl-1-nitrosourea)); cisplatin; bleomycin.

3) DBPT which consists of: DTIC; BCNU, cisplatin, tamoxifen.

4) BELD which consists of: bleomycin, eldisine, CCNU, DTIC.

5) DVC which consists of: DTIC, Vindesine, cisplatin.

6) POC which consists of: procarbazine, vincristine and CCNU.

However, the overall response rate to these combination therapies ranges from 27–52% (McClay and Mastrangelo, *Seminars in Oncology* 15: 569–77, 1988). Thalidomide has been used as a single therapeutic agent or in combination therapy to treat a number of immunologically based diseases such as: aphthous ulcers (Jenkins et al., *Lancet* 2: 1424–6, 1984; Grinspan, *J. Amer. Acad. Dermatol* 12: 85–90, 1985; Revuz et al., *Arch. Dermatol* 126: 923–7, 1990), Graff vs Host Disease (Lim et al., *Lancet* 1: 117, 1988; McCarthy et al., *Lancet* 2: 1135, 1988; Henley et al., *Lancet* 2: 1317, 1988), erythema nodosum leprosum (Sheskin, *Lepr. Rev.* 36: 1837, 1965; Sheskin and Convit, *Int. J. Lepr.* 37: 135–46, 1969; Pearson and Vedagiri, *Lepr. Rev.* 40: 111–6, 1969), Behcets Disease (Saylan and Saltik, *Arch. Dermatol* 118: 536, 1982; Jorizzo et al., *Arch. Int. Med.* 146: 878–81, 1986), actinic prurigo (Londono, *Int. J. Dermatol* 12: 326–8, 1973; Lowell et al., *Brit. J. Dermatol* 108: 467–71, 1983) and ulcerative colitis (Waters et al., *Brit. Med. J.* 1: 792, 1979) and discoid lupus erythematosus (Knop et al., *Arch. Dermatol Res.* 271: 165–70, 1981). In these studies dosages ranging form 100 mg/day to 800 mg/day were administered without serious side effects.

In light of the seriousness of the disease and the paucity of effective therapeutic agents to treat malignant melanomas, there exists a need to develop a therapeutically-effective protocol for the treatment of melanomas.

The prior art is silent regarding the use of thalidomide alone or in combination with other anti-melanoma agents to treat melanomas.

Furthermore, the prior art is silent regarding the use of thalidomide alone or in combination with other agents to inhibit the production and/or action of cytokine/growth factors such as M-alpha, IGF-1, EGF, TGF alpha, IL-1 beta, MGSA and bFGF in different cell types involved in tumor growth and/or angiogenesis of melanoma.

SUMMARY OF THE INVENTION

The primary objective of the present invention is to provide a method for the treatment of melanoma with cytokine/growth factor inhibitors.

A further objective of the present invention is the treatment of melanomas with thalidomide alone or in combination with other agents that inhibit cytokine/growth factors, and/or with other classes of anti-melanoma therapeutics.

Another object of the current invention is to provide a method for treating melanoma with thalidomide at a given regimen.

A further objective is to use thalidomide alone or in combination with other therapeutics to prevent establishment of cancer at secondary body sites during or after primary therapy for melanoma.

A further objective to use thalidomide alone or in combination with other therapeutics to prevent a relapse of melanoma at a later time.

A still further objective is to use thalidomide alone or in combination with other therapeutics to act as a prophylactic agent to prevent melanoma in those patients considered at risk.

An additional objective of the current invention is to provide compositions of matter comprising cytokine growth factor inhibitors with agents of other classes of anti-melanoma therapeutics.

A still further objective of the present invention is a method for the therapeutic treatment of melanomas which comprises treatment with thalidomide and other drugs on alternative days by diverse schedules.

DESCRIPTION OF THE PREFERRED EMBODIMENTS

The present invention deals with a method for treating melanomas in a mammal in need of such treatment, said method comprising administering to said mammal an amount of thalidomide effective in the treatment of melanomas.

Additionally, the instant invention relates to a method for treating melanomas in a mammal in need of such treatment, said method comprising administering to said mammal a therapeutically-effective amount of a cytokine/growth factor inhibitor selected from the group consisting of basic fibroblast growth inhibitors, TNF alpha inhibitors, interleukin-1 inhibitors, IGF-1 inhibitors, EGF inhibitors, TGF alpha inhibitors and melanoma growth stimulatory activity (MGSA) factor inhibitors to cause regression of the melanoma.

Furthermore, the present invention provides a method for treating a mammal afflicted with melanoma which comprises administering a therapeutically effective amount of thalidomide in combination with other anti-melanoma drugs to cause regression of the melanoma.

As used herein, the term "therapeutic" treatment refers to administration of thalidomide alone or in combination with other anti-melanoma drugs to a patient after the patient has been diagnosed or having melanoma.

As used herein, the term "pharmaceutically acceptable" refers to a carrier medium that does not interfere with the effectiveness of the biological activity of the active ingredient(s), is chemically inert, and is not toxic to the human patients to whom it is administered.

The term "therapeutic cycle" when used in the present specification, refers to a 28-day or other cycle wherein thalidomide or a combination of thalidomide with other anti-melanoma agents is administered to the patient. Two or more cycles of the therapy is referred to herein as the "therapeutic regimen." Escalating dosages of thalidomide may be administered in each successive cycle. Escalating dosages of thalidomide are generally dependent on response and level of toxicity observed for each individual.

The administration of thalidomide may take place by any suitable technique, including parenteral administration. Examples of parenteral administration include intravenous, intraarterial, intramuscular, subartaneous, and intraperitoneal. Oral administration is the most common form of administration.

The dose and dosage regimen will depend mainly on the degree of malignancy, the patient, the patient's history, and his/her response to prior treatment. The amount must be effective to result in clinical improvement or in vitro evidence of immune function augmentation or both. The dose of thalidomide or combinations of thalidomide with other anti-melanoma agents may be single doses or multiple doses. If multiple doses are employed, the frequency of administration will depend on the patient, type of tumor response, dosage amounts, etc.

Administration once a week may be effective, wherein for other, daily administration or administration every other day or every third day may be effective. The practitioner will be able to ascertain upon routine experimentation in conjunction with the teaching if the following examples, which route of administration and frequency of administration are most effective in any particular case as in every call, to augment cellular immune function in vitro and/or improve clinical signs.

The dosage amount that appears to be most effective herein is one that results in remission, no appearance, or decreased tumor burden and is not toxic or is acceptably toxic to the patient, as defined by the protocol in the Examples below. Generally, such conditions as fever, chills, and general malaise are considered acceptable. This optimum dose level will depend on many factors, for example, on the type of patient, the response of the patient, the type of tumor, route and schedule of administration, existing tumor burden, and the definition of toxicity. Toxicity to the human patient may be defined by the extent and type of side effects, with fever, chills, and general malaise considered acceptable toxicity for purpose herein.

The invention also provides pharmaceutical compositions comprising thalidomide, an anti-melanoma therapeutic agent and a pharmaceutical inert carrier.

The anti-melanoma drugs are selected from the group consisting of Dacarbazine (DTIC), Carmustine (BCNU-1, 3-bis-[2-chloroethyl- 1-nitrosourea), cisplatin, tamoxifen, lomustine (CCNV-1- [2-chloroethyl] 3-cyclohexyl-1-nitrosourea), bleomycin, eldisine, vindesine, procarbazine and vincristine.

When used alone, the therapeutically effective amounts of thalidomide are typically 50 mg to 1000 mg and preferably 100 mg to 750 mg two or three times a day for a period of time to induce shrinkage or remission of the melanoma.

Under certain circumstances, it is desirable to administer thalidomide therapy simultaneously with other anti-melanoma drugs. For example, 500 mg of thalidomide can be administered three times a day while the patient is being given a chemotherapeutic treatment with carmustine, i.e., 150–200 mg/m$^2$ every six weeks. If Lomustine is given orally, typically 130 mg/m$^2$, in a single oral dose is given every six weeks while the patient is in thalidomide therapy. When bleomycin is the drug of choice, 10 to 20 units/m$^2$ is given weekly or twice weekly. If cisplatin is the drug of choice, 20 mg/m$^2$ IV is given daily for five days every three weeks. The therapy with all of the above chemotherapeutic compounds is given simultaneously with thalidomide. In an alternate embodiment, thalidomide is administered every other day.

Additionally, applicants propose to use thalidomide alone or in combination with other cytokine/growth factor inhibitor therapies to treat melanoma. An example of such a combination therapy utilizes thalidomide given with pentoxyphylline and a glucocorticoid such as dexamethasone. The activity of each of these agents would be expected to enhance that of the other two in inhibiting TNF alpha synthesis since each of these agents acts as an inhibitor at a different point in this synthesis. Pentoxyfylline inhibits TNF alpha gene transcription, while thalidomide enhances TNF alpha m-RNA degradation and glucocorticoids such as dexamethasone inhibit TNF alpha m-RNA translation.

The precise amount of thalidomide alone or with other chemotherapeutic agents mentioned above will vary depending, for example, on the condition for which the drug is administered and the size and kind of the mammal. Generally speaking the thalidomide can be employed in any amount effective in the treatment of melanomas.

For humans, typically effective amounts of thalidomide for use in the unit dose compositions of the present invention range from 50 mg to 2000 mg per 24 hours; however, greater amounts may be employed if desired. This range is based on administration to a 70 kg human. A preferred amount is less than 1500 mg per 24 hour period. Of course the amounts of each compound selected will depend on the weight of the mammal and the disease state. One skilled in the art can adjust the dosage forms to achieve the desired therapeutic levels.

The compound of the present invention can be prepared and administered in a wide variety of oral dosages and dosages administered by other routes. It will be obvious to those skilled in the art that the following dosage forms may comprise as the active component either thalidomide alone or in combination with other compounds. Preferably the compounds of the present invention are administered orally, intramuscularly, topically, subcutaneously, or intravenously.

For preparing pharmaceutical compositions from the compounds of the present invention, pharmaceutically acceptable carriers can be either solid or liquid. Solid form preparation include powders, lotions, creams, ointments, tablets, pills, capsules, cachets, suppositories, and dispensable granules. A solid carrier can be one or more substances which may also act as diluents, flavoring agents solubilizers, lubricants, suspending agents, binders, preservative, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methycellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills cachets, and lozenges can be used as solid dosage forms suitable for oral administration.

For preparing suppositories, low melting wax, such as mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations such as lotions or creams include solutions, suspensions, and emulsions, for example, water or water propylene glycol solutions. For parenteral injection, liquid preparations can be formulated in solution in aqueous polyethylene glycol solution.

Solutions suitable for oral use can be prepared by dissolving the active component in an appropriate fluid and adding suitable colorants, flavors, stabilizing, and thickening agents as desired.

Liquid suspensions suitable for oral use can be made by dispersing the finely divided active component in an appropriate liquid with viscous material, such as natural or synthetic gums, resins, methycellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, lotions and powders in vials or ampoules. Also, the unit dosage form can be a capsule, tablet, cachet, or lozenge itself, or it can be the appropriate number of any of these in packaged form.

It is also possible to administer thalidomide in a time-release formulation. A wide variety of methods are now available in the art for preparing time-release or long-acting compositions. Any of these time-release or long-acting formulations are suitable in the practice of the present invention as long as it does not adversely affect the effectiveness of the thalidomide in the treatment of melanomas. Advantages of time-release formulations include a lower concentration of peak serum absorption which substantially reduces the adverse side effects and toxicity of the compound administered. In addition, a reduced frequency of administration results, which substantially improves patient compliance. A frequency of administration of every 12 or 24 hours would be preferred. In addition, more constant serum concentration of thalidomide would result thereby allowing a more consistent relief of symptoms.

The following examples, not to be construed as limiting, illustrate formulations which can be made according to the invention.

EXAMPLE 1

500 mg of thalidomide are mixed with 130 mg of Lomustine. The active ingredients are triturated and q.s. with lactose to selected capsules size.

EXAMPLE 2

500 mg of thalidomide are mixed with 200 mg of Lomustine. The active ingredients are triturated and q.s. with lactose to selected capsule size.

EXAMPLE 3

250 mg of thalidomide are mixed with 130 mg of Lomustine. The active ingredients are triturated and q.s. with lactose to selected capsule size.

EXAMPLE 4

Hard gelatin capsules are prepared using the following ingredients

|  | Quantity (mg/capsules) |
| --- | --- |
| Thalidomide | 250 |
| Starch dried | 200 |
| Magnesium stearate | 10 |

The above ingredients are mixed and filled into hard gelatin capsules in 460 mg quantities.

EXAMPLE 5

A tablet formula is prepared using the ingredients below

|  | Quantity (mg/tablet) |
| --- | --- |
| Thalidomide | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 6

Tablets each containing 60 mg of active ingredients are made up as follows:

| Thalidomide | 60 mg |
| --- | --- |
| Starch | 45 mg |
| Microcrystalline cellulose | 35 mg |
| Polyvinylpyrrolidone (as 10% solution in water) Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed by a tablet machine to yield tablets each weighing 150 mg.

EXAMPLE 7

Capsules each containing 80 mg of medicament are made as follows:

| Thalidomide | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 8

Suspensions each containing 50 mg of medicament per 5 ml dose are made as follows:

| Thalidomide | 50 mg |
| --- | --- |
| Sodium carboxymethylcellulose | 50 mg |
| Syrup | 1.25 ml |
| Benzoic acid solution | 0.10 ml |
| Flavor | q.v. |
| Color | q.v |
| Purified water to | 5 ml |

The medicament is passed through a No. 45 mesh U.S. sieve, and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 9

Capsules each containing 150 mg of medicament are made as follows:

| Thalidomide | 150 mg |
| --- | --- |
| Starch | 164 mg |
| Microcrystalline cellulose | 164 mg |
| Magnesium stearate | 22 mg |
| Total | 500 mg |

The active ingredient, cellulose, starch, and magnesium stearate are blended, passed through a No. 45 mesh U.S. sieve, and filled into hard gelatin capsules in 500 mg quantities.

EXAMPLE 10

A topical ointment containing thalidomide is prepared as follows:

|  | % by weight |
| --- | --- |
| Thalidomide | 20% |
| Vegetable oil | 10% |

-continued

| | % by weight |
|---|---|
| Acetyl lanolin | 10% |
| Lanolin alcohol | 12% |
| Sorbital sesquioleate | 20% |
| Water add | 100% |

EXAMPLE 11

A gel is made as follows:

| | % by weight |
|---|---|
| Thalidomide | 15% |
| Carboxyvinyl polymers | 2% |
| Preservative | 0.01% |
| Water add | 100% |

EXAMPLE 12

An unguent has the following composition:

| | |
|---|---|
| Thalidomide | 6.0 g |
| Stearyl alcohol | 3.0 g |
| Lanoline | 5.0 g |
| Vaseline | 15.0 g |
| Distilled water to make up to | 100.0 g |

EXAMPLE 13

Liposomes containing thalidomide are made as follows:

Solutions of lecithin, cholesterol, and an active ingredient in chloroform/ethanol(1:1) or in chloroform/methanol (1:1) are evaporatively concentrated at about 30 degrees Centigrade in a rotary evaporator, whereby a thin film of lipid and active ingredients forms. Then 8M calcium chloride solution at 60 degrees Centigrade is added to the film, and the liposomes are separated from the wall by manual shaking. The resulting dispersion is then placed in an ultrasonic disintegrator to produce smaller particle sizes and is centrifuged. The combination of liposomes and active ingredient is then washed three times with calcium chloride solution.

Liposomes containing approximately 25–40% by weight are accordingly obtained.

EXAMPLE 14

Ointment containing thalidomide:

| | |
|---|---|
| Thalidomide | 1.0 g |
| Isopropyl myristate | 81.7 g |
| Liquid petrolatum oil | 9.1 g |
| Silica - aerosol 200 | 9.18 g |

EXAMPLE 15

CLINICAL APPLICATION OF THE INVENTION

A. PATIENT ELIGIBILITY

Patients between 18 to 70 years of age are admitted to the study. Each patient has to meet the following criteria for entering the study:

1. A histologically confirmed, primary diagnosis of Stage III or Stage IV (disseminated) melanoma.
2. Measurable disease by physical examination or by noninvasive radiologic procedure.
3. A Karnofsky performance score of 70 or greater.
4. Serum creatinine less than 2.0 mg/100 ml; bilirubin less than 1.5 mg/100 ml; SGPT less than 50 IU/L.
5. Granulocyte count greater than 1500/mm$^3$; total WBC count greater than 3000/mm$^3$; platelet count greater than 100,000/mm$^3$; prothrombin time less than 1.3× control.
6. A minimum life expectancy of four months.
7. The ability to give written informed consent, which must be obtained prior to treatment.

PERFORMANCE STATUS CRITERIA

| ECOG | Karnofsky |
|---|---|
| 0 - Normal activity | 100 - Normal; no complaints |
| 1 - Symptoms but ambulatory | 90 - Able to carry on normal activities; minor signs or symptoms of disease. |
| 2 - In bed less than 50% of time | 80 - Normal activity with effort. |
| | 70 - Cares for self. Unable to carry on normal activity or to do active work. |
| | 60 - Ambulatory. Requires some assistance in activities of daily living and self-care. |
| 3 - In bed more than 50% of time | 50 - Requires considerable assistance and frequent medical care. |
| | 40 - Disabled; requires special care and assistance. |
| 4 - 100% bedridden | 30 - Severely disabled; hospitalization indicated though death not imminent. |
| | 20 - Very sick; hospitalization and active supportive treatment. |
| | 10 - Moribund |
| | 0 - Dead |

Patients with any of the following are excluded from these studies:

1. Serious active infections requiring antibiotic therapy, or other serious intercurrent illness, or past history of any serious opportunistic infections not related to myelosuppressive toxicity.
2. Pregnant or lactating women; women of childbearing potential unless using effective contraception.
3. Participation in another experimental clinical trial within three weeks of entry into the present study.
4. CNS metastases, CNS infection (including retinal disease), vasculitis, a known seizure disorder, or a concurrent malignancy in addition to melanoma.
5. Patients who have received:
   a. Chemotherapy, hormonal therapy, immunotherapy or radiation therapy within three weeks prior to study entry (6 weeks for nitrosureas or mitomycin C).
   b. Patients who have received DTIC in the past.
6. Patients not considered fully recovered from any prior surgical treatment.
7. Patients with major organ allografts.
8. Patients with history or current evidence of cardiac disease unless they are NY Heart Association Class IA and have a normal stress test.
9. Patients currently participating in another clinical trial (excluding studies using approved antibiotics).

B. TREATMENT PROTOCOLS

1. Dose and schedule—On the average, typically twenty patients are admitted and treated with 2, 3, or 4 cycles of thalidomide. Each cycle is conducted for 7, 21 or 28 days depending on the degree of malignancy. All drugs are administered by hospital staff either while in-patient or in the our-patient clinic. Patients typically one given 500 mg of thalidomide three times a day.

For the first cycle—Patients are given large initial doses of thalidomide 500 mg three times a day for seven days.

For the second cycle—In the absence of disease progression and Grade III toxicity during cycle, the dose may be escalated to 750 mg three times a day for seven days.

For the third cycle—In the absence of disease progression and grade III toxicity, the dose is identical to treat given in cycle two and it given for seven days.

It should be noted that cycles are selected depending on the condition of the patient, presence of adverse events, and severity of the disease.

DURATION OF THERAPY

Patients who had achieved a complete response upon completion of the first three cycles may repeat an additional two cycles beyond documentation of response and then be observed for duration of response.

Patients who had a partial response upon completion of the first three cycles of therapy may continue therapy until complete response occurs or until disease progression or toxicity intervenes. If a complete response is achieved, they may repeat an additional two cycles beyond documentation of response and then be observed for duration of response.

EXAMPLE 11

COMBINATION THERAPY

A. DOSE AND SCHEDULE

Patients will receive three cycles of thalidomide therapy in combination with Lomustine. Each cycle from Lomustine is 28 days and the drug is administered at 130 mg/m$^2$ in a single oral dose. During this cycle thalidomide is administered at a dosage of 500 mg three times a day for 14 days immediately after Lomustine administration. Cycles 1, 2, and 3 are conducted at the above dosage levels and variations in thalidomide dosages may be adjusted depending on disease progression.

Patients who have progression disease or no change upon completion on the first three cycles are removed from the study.

DURATION OF THERAPY

Patients who have achieved a complete response upon completion of the first three cycles may repeat an additional two cycles beyond documentation of response and then be observed for duration of response.

Patients who have a minor or partial response upon completion of the first three cycles of therapy may continue therapy until complete response occurs or until disease progression or toxicity intervenes. If a complete response is achieved, they may repeat an additional two cycles beyond documentation of response and then be observed for duration of response. If the response becomes stabilized without a complete response being achieved, patients will be removed from active treatment but continued on study until disease progression.

It is to be understood that the forms of the invention herein are to be taken as preferred examples of the same, and that various changes may be made without departing from the spirit of the invention or scope of the subjoined claims.

What is claimed is:

1. A method for the treatment of melanoma in a mammal having said disease which comprises administering to said mammal an enhanced therapeutically effective amount of thalidomide in combination with an effective amount of lomustine to cause regression of the melanoma.

2. A pharmaceutical composition of matter for treating melanoma in a mammal in need of such treatment, said composition comprising an enhanced effective amount of thalidomide and lomustine and a pharmaceutical inert carrier.

* * * * *